(12) United States Patent  
Berggren et al.

(10) Patent No.: US 9,351,511 B2  
(45) Date of Patent: May 31, 2016

(54) METHOD FOR MODIFYING POLYPHENOL CONTAINING PLANT MATERIALS AND MEDICAL USES OF MODIFIED POLYPHENOL PLANT CONTAINING MATERIALS

(75) Inventors: Anna Berggren, Flyinge (SE); Jan Alenfall, Lomma (SE); Mikael Nilsson, Hjarup (SE); Inger Bjorck, Lund (SE); Yvonne Granfeldt, Lund (SE)

(73) Assignee: PROBI AB, Lund (SE)

( * ) Notice: Subject to any disclaimer, the term of this patent is extended or adjusted under 35 U.S.C. 154(b) by 931 days.

(21) Appl. No.: 12/663,688

(22) PCT Filed: Jun. 5, 2008

(86) PCT No.: PCT/SE2008/000383  
§ 371 (c)(1),  
(2), (4) Date: Apr. 15, 2010

(87) PCT Pub. No.: WO2008/150212  
PCT Pub. Date: Dec. 11, 2008

(65) Prior Publication Data  
US 2010/0280132 A1  Nov. 4, 2010

(30) Foreign Application Priority Data  
Jun. 8, 2007  (SE) ...................................... 0701440

(51) Int. Cl.  
*A61K 36/45*  (2006.01)  
*A23L 1/105*  (2006.01)  
(Continued)

(52) U.S. Cl.  
CPC ............. *A23L 1/3014* (2013.01); *A23L 1/3002* (2013.01); *A61K 35/747* (2013.01); *A61K 36/00* (2013.01); *A23V 2002/00* (2013.01); *A61K 2236/19* (2013.01)

(58) Field of Classification Search  
CPC ..... A23L 1/3014; A23L 1/105; A23L 1/3002; A61K 35/474; A61K 36/00  
See application file for complete search history.

(56) References Cited

U.S. PATENT DOCUMENTS 6,214,336 B1 * 4/2001 Bukowska ........... A61K 35/747  
424/93.45  
6,641,852 B2 * 11/2003 Wang et al. ..................... 426/46  
(Continued)

FOREIGN PATENT DOCUMENTS

CN  1947533 A  4/2007  
EP  0554562 A1  8/1993  
(Continued)

OTHER PUBLICATIONS

Changhon et al. Green Tea Polyphenols Modulate Insulin Secreation by Inhibiting Glutamate Dehydrogenase; The Journal of biological Chemistry, vol. 281, No. 15 pp. 10214-10221.*

(Continued)

*Primary Examiner* — Patricia A Leith  
(74) *Attorney, Agent, or Firm* — Knobbe, Martens Olson & Bear, LLP

(57) ABSTRACT

The present invention relates to a method for modifying polyphenol containing plant material(s), wherein said method comprises: mixing at least one polyphenol containing material and at least one solvent to provide a mixture; heating the mixture to eliminate bacterial species present to provide a heated mixture; adding at least one polyphenol modifying strain of lactic acid bacteria and optionally at least one protein source, in optional order or simultaneously, to the heated mixture to provide a fermentation mixture; and subjecting the fermentation mixture to conditions suitable for fermentation of the fermentation mixture to provide a mixture of modified polyphenol containing plant material(s); and optionally eliminating the polyphenol modifying strain of lactic acid bacteria to provide a mixture of modified polyphenol containing plant material(s) free from living lactic acid bacteria.

8 Claims, 7 Drawing Sheets

(51) Int. Cl.
   *A23L 1/30*   (2006.01)
   *A61K 35/747*  (2015.01)
   *A61K 36/00*   (2006.01)

(56) References Cited

U.S. PATENT DOCUMENTS

| | | | |
|---|---|---|---|
| 7,891,290 B1* | 2/2011 | Chatterjee et al. | 99/453 |
| 8,685,446 B2* | 4/2014 | Casana-Giner | B01J 13/18 424/451 |
| 2003/0185811 A1* | 10/2003 | Teasdale et al. | 424/93.45 |
| 2005/0255126 A1* | 11/2005 | Tsubaki et al. | 424/195.16 |
| 2008/0102132 A2* | 5/2008 | Giner | B01J 13/18 424/490 |
| 2008/0286254 A1* | 11/2008 | Sakamoto | A23D 9/007 424/93.45 |
| 2009/0035416 A1* | 2/2009 | Shimizu | A23C 9/1234 426/43 |
| 2010/0280132 A1* | 11/2010 | Berggren | A61K 36/00 514/731 |

FOREIGN PATENT DOCUMENTS

| | | | |
|---|---|---|---|
| JP | 11-276072 A | | 10/1999 |
| JP | 2002-335881 A | | 11/2002 |
| JP | 2003047400 A | * | 2/2003 |
| JP | 2004-520276 A | | 7/2004 |
| JP | 2005-278517 A | | 10/2005 |
| WO | WO 02/38165 A1 | | 5/2002 |
| WO | WO 2004087893 A1 | * | 10/2004 |
| WO | WO 2004/101770 A1 | | 11/2004 |
| WO | WO 2006/035218 A1 | | 4/2006 |

OTHER PUBLICATIONS

Dixon et al.: Improvements in Insulin Sensitivity and Beta-Cell Function (homa) With Weight Loss in the Severely Obese; Diabetic Medicine, (2003), 20, pp. 127-134.*

Mizuno et al. Type 2 Diabetes and Oral Antiyperglycemic Drugs: Current Medicinal Chemistry, 2008, 15, pp. 61-74.*

Song et al.: Effect of Momordica Grosvenori on Oxidative Stress Pathways in Renal Mitochondria of Normal and Alloxan-Induced Diabetic Mice; Eur J Nutr (2007), 46, pp. 61-69.*

Thompson, C. Animal Models of Diabetes Mellitus; Relevance to Vascular Complications;Current Pharmaceutical Design; 2008, 14, pp. 309-324.*

Wang et al. Mechanisms and Outcomes of Drug and Toxicant Induced Liver Toxicity in Diabetes; Critical Reviews in Toxicology; Boca Raton; Jun. 2007, vol. 37, Iss. 5, pp. 413-459.*

Cooke et al. Nature Reviews; Drug Discovery, vol. 5, Nov. 2006, pp. 919-931.*

Molin Probiotics in Foods Not Containing Milk or Milk Constituents, With Special Reference to Lactobacillus Plantarum 299v 1-3; The American Journal of Clinical Nutrition; 2001 vol. 73, No. 2 380s-385s.*

Birt, N. ((2011) Phytochemical Optimization of Blueberry Juice; (Masters Thesis); Massey University; Palmerston North, NZ; pp. 12 and 16, accessed from Massey Research Online, URLhttp://mro.massey.ac.nz/bitstream/handle/10179/3235/02_whole.pdf?sequence=1 on Oct. 8, 2014).*

Chen, X. May 31, 2002 "Study of the Metabolic Mechanism of Catechine during the fermentation of green tea and the biological activity of the resulting product" Zhejiang University Master Thesis.

Chinese State Intellectual Property Office of the Peoples Republic of China Office Action in Chinese Patent Application No. 200880019313.4, Issued May 18, 2011.

Chinese State Intellectual Property Office of the Peoples Republic of China Office Action in Chinese Patent Application No. 200880019272.9, Issued Jul. 19, 2011.

He, J.-D. 2002 "Application of microwave to pyrogenation of coal gangue for solid polyaluminum chloride" Coal Mine Environmental Protection 16(6): pp. 20, 21 and 30.

Johnston, K.L. et al. 2002 "Possible role for apple juice phenolic compounds in the acute modification of glucose tolerance and gastrointestinal hormone secretion in humans" *Journal of the Science of Food and Agriculture* 82:1800-1805.

Martin, L.J. et al. 2005 "Increase of antioxidant capacity of the lowbush blueberry (*Vaccinium angustifolium*) during fermentation by a novel bacterium from the fruit microflora" *Journal of the Science of Food and Agriculture* 85:1477-1484.

Neto, C.C. 2007 "Cranberry and blueberry: Evidence for protective effects against cancer and vascular diseases" *Mol. Nutr. Food Res.* 51:652-664.

Salminen, J.P. et al. 1999 "Characterisation of hydrolysable tannins from leaves of Betula pubescens by high-performance liquid chromatography—mass spectrometry" *J Crom A* 864:283-291.

Salminen, J.P. et al. 2005 "Characterisation of proanthocyanidin aglycones and glycosides from rose hips by high-performance liquid chromatography-mass spectrometry, and their rapid quantification together with vitamin C" *J Crom A* 1077:170-180.

Zunino, S.J. et al. 2007 "Diets Rich in Polyphenols and Vitamin A Inhibit the Development of Type I Autoimmune Diabetes in Nonobese Diabetic Mice" *The Journal of Nutrition* 137:1216-1221.

Office Action in related Japanese Patent Application No. 2010-511143, dated Mar. 21, 2013.

Granfeldt, Y.E. and Bjorck, I.M.E. et al. 2011 "A bilberry drink with fermented oatmeal decreases postprandial insulin demand in young healthy adults" Nutrition Journal 10: 57 (10 pages).

* cited by examiner

US 9,351,511 B2

METHOD FOR MODIFYING POLYPHENOL CONTAINING PLANT MATERIALS AND MEDICAL USES OF MODIFIED POLYPHENOL PLANT CONTAINING MATERIALS

RELATED APPLICATIONS

This application is a U.S. National Phase of International Application No.: PCT/SE2008/000383, filed Jun. 5, 2008, designating the U.S. and published in English on Dec. 11, 2008 as WO 2008/150212, which claims the benefit of Swedish Application No. 0701440-0, filed Jun. 8, 2007.

TECHNICAL FIELD OF THE INVENTION

The present invention relates to a method for modifying polyphenol containing plant material(s) and to novel medical uses of different modified polyphenol containing plant material(s).

TECHNICAL BACKGROUND

The World Health Organisation (WHO) predicts that 300 million people (~5% of today's population) will have developed type 2 diabetes in 2025. This means that a considerable amount of the population will suffer from various metabolic disturbances, such as the metabolic syndrome. The term "metabolic syndrome" has been debated, both as a clinical diagnosis and as a definition. Still it represents an alarming group of metabolic risk factors that identifies subjects at high risk of developing type 2 diabetes and cardiovascular disease.

Today there are three major criteria that are commonly accepted by the International Diabetes Federation (IDF) and the World Health Organisation (WHO), those are measures of obesity, dyslipidaemia and insulin resistance. Each one of these risk factors is good predictor of cardiovascular disease. However, insulin resistance is considered as a key component of the metabolic syndrome since it predicts both type 2 diabetes and cardiovascular disease. Insulin secretion is necessary not only for maintaining glucose metabolism, but also for controlling lipid metabolism and vascular tone. Insulin resistance results in an imprecise regulation of the beta cells to maintain euglycaemia, leading to hyperinsulinaemia, which in turn severs the insulin resistance in major metabolic tissues and organs, like muscle, adipose tissue and liver and a vicious circle between insulin resistance and hyperinsulinaemia develops. The cause of insulin resistance is not fully understood and there are several genetic predispositions (genetic inheritance, polymorphisms), molecular factors, such as oxidative stress and various markers of inflammation that may interfere with insulin signaling.

Last but not least is the major impact of intensive lifestyle modifications, which in intervention studies have been found to delay or prevent the development of type 2 diabetes by 40-58%. The diet in these intervention studies aimed at weight reduction by reducing energy intake from fat, above all from saturated fat (partially replaced by monounsaturated fat) and was additionally rich in fiber, whole grain, vegetables, and fruits. The diet restrictions were accompanied by 30 min of physical activity a day. Physiological benefits with intensive lifestyle modifications are decreased body weight and blood pressure and improvements in insulin sensitivity and blood lipids. This will affect the whole spectrum of risk components and has been found to delay or prevent the development of diseases related to the metabolic syndrome.

In view of the above it is not surprising that a lot of effort has been engaged in the research of the mechanisms behind the above mentioned diseased as well as to find new ways to prevent, alleviate or treat these diseases.

Foods causing low insulin responses are considered favorable since high insulin levels (hyperinsulinemia) after a meal are risk factors for the development of diseases within the metabolic syndrome (cardiovascular diseases, type 2 diabetes and obesitas). Thus, foods causing lower insulin levels in the human body would be beneficial to humans in the industrialized part of the world where problems with cardiovascular diseases such as type 2 diabetes, obesitas and the metabolic syndrome are growing.

In accordance with the present invention, novel ways to treat and prevent such diseases have been found.

SUMMARY OF THE INVENTION

The present invention provides, in one aspect, a method for modifying polyphenol containing plant material(s), wherein said method comprises:
a) mixing at least one polyphenol containing material and at least one solvent to provide a mixture;
b) heating the mixture to eliminate bacterial species present to provide a heated mixture;
c) adding at least one polyphenol modifying strain of lactic acid bacteria and optionally at least one protein source, in optional order or simultaneously, to the heated mixture to provide a fermentation mixture; and
d) subjecting the fermentation mixture to conditions suitable for fermentation of the fermentation mixture to provide a mixture of modified polyphenol containing plant material(s); and
a) optionally eliminating the polyphenol modifying strain of lactic acid bacteria to provide a mixture of modified polyphenol containing plant material(s) free from living lactic acid bacteria.

The present invention provides, in a further aspect, the use of a mixture of modified polyphenol containing plant material(s) comprising living lactic acid bacteria or a mixture of modified polyphenol containing plant materials) free from living lactic acid bacteria, for the manufacture of a composition for the prevention or treatment of diabetes, the metabolic syndrome, cardiovascular diseases.

DETAILED DESCRIPTION OF EMBODIMENTS OF THE INVENTION

Figure 1:
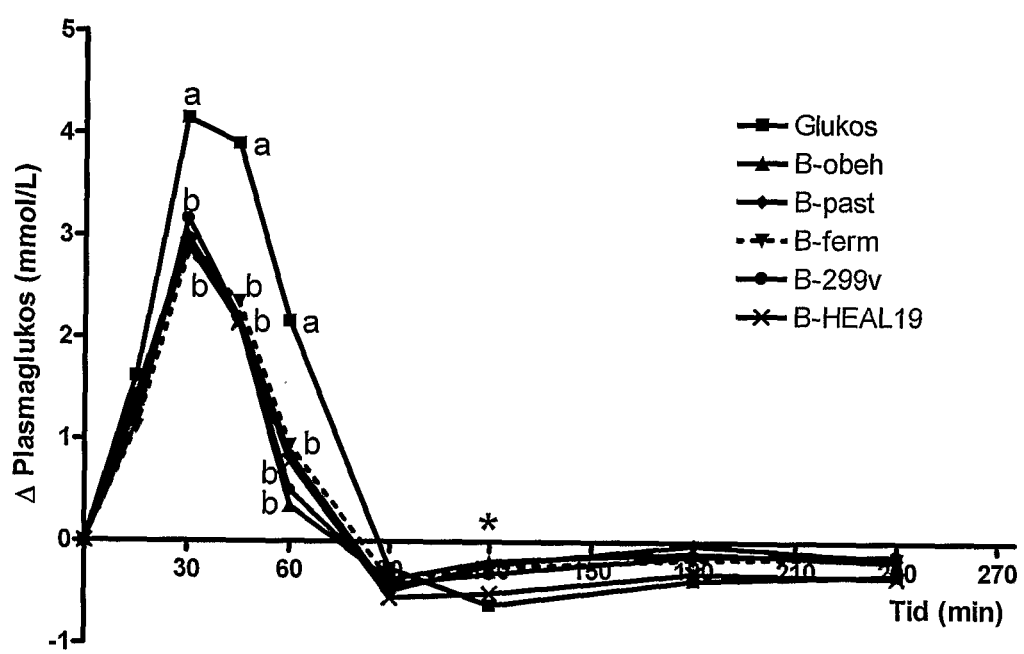
FIG. 1 shows the postprandial plasma glucose curves obtained after intake of different blueberry drinks by test individuals in relation to a glucose reference drink.

In an embodiment of the method of invention, the mixture of the at least one polyphenol containing plant material and the at least one solvent is obtained by homogenization. The solvent is preferably water, tap water or distilled water, but could be another aqueous edible solvent such as mineral water, juices, such as fruit juices and vegetable juices, milk and other drinks.

In order to eliminate any bacterial species such as bacteria and/or microorganisms present in the prepared mixture of the at least one polyphenol containing material and the at least one solvent, in order to prevent any growth of the same, the heating in step b) takes place at a temperature of 60° C.-100° C., preferably 80° C.-100° C., more preferably 90° C.-100° C., i.e. a temperature sufficient to kill bacteria and microorganism, e.g. pasteurization at 94° C. for 2 s or using a conventional autoclave to eliminate the bacteria present. The fermentation as provided in step d) should only take place for the specific strain of lactic acid bacteria as added to the mixture. Therefore, it is necessary to eliminate any other species of bacteria as may be present in the heating step b) before the fermentation. The heating temperature and duration of heating are decided in view of the desired result, i.e. to kill any bacteria and microorganisms present.

After the heating step b), the pH of the heated mixture could be adjusted to a pH value in the range of about 4.5-9, preferably 5-7, e.g. by addition of KOH since the polyphenol containing material could be acidic. This is because the added strain of lactic acid bacteria will grow well at this pH interval. The at least one polyphenol modifying strain of lactic acid bacteria is added in an amount of about $10^5$-$10^9$ cfu/ml mixture. Preferably, the fermentation takes place in the presence of at least one protein source, e.g. an amino acid source, said protein source being chosen, but not limited, to the group comprising peptones, tryptones (milk broth), yeast extracts and combinations thereof. Another example is meat broth or oatmeal, which also comprise the necessary components for the bacteria. It is also possible that the fermentation takes place, without the addition of a protein source, i.e. in the presence of only the components of the added polyphenol containing plant material(s), i.e. present proteins and carbohydrates in these plant materials. The at least one protein is added or present in amount of 0.0001-0.1% by weight of the total mixture.

In an embodiment of the invention, said at least one polyphenol modifying strain of lactic acid bacteria is chosen from the group comprising *Lactobacillus, Pediococcus, Streptococcus, Weissella, Leuconostoc, Oenococcus, Lactococcus* and phylogenetically related genera. In another embodiment of the invention said at least one polyphenol modifying strain of *Lactobacillus* is chosen from the group comprising *Lactobacillus plantarum, Lactobacillus paraplantarum, Lactobacillus pentosus*, and *Lactobacillus argentoratensis*.

Preferably, the *Lactobacillus plantarum* is chosen from the group of strains consisting of *Lactobacillus plantarum* 299, DSM 6595, which was deposited on 2 Jul. 1991 at the Deutsche Sammlung von Mikroorganismen und Zellkulturen GmbH, *Lactobacillus plantarum* 299v, DSM 9843, which was deposited on 16 Mar. 1995 at the Deutsche Sammlung von Mikroorganismen und Zellkulturen GmbH, *Lactobacillus plantarum* HEAL 9, DSM 15312, *Lactobacillus plantarum* HEAL 19, DSM DSM 15313, and *Lactobacillus plantarum* HEAL 99, DSM 15316, which were deposited on Nov. 27, 2002, at the Deutsche Sammlung von Mikroorganismen and Zellkulturen GmbH and were then given the accession numbers referred to above.

After the addition of the specific strain of lactic acid bacteria the fermentation conditions are at a temperature of approximately 30° C.-50° C., preferably approximately 35° C.-45° C., especially approximately 37° C.-40° C., in a liquid medium at atmospheric pressure. The fermentation is usually proceeded until a pH value of <5, preferably <4, is reached. If a yoghurt is fermented the fermentation is continued to pH<4.6-4.7. The fermentation takes place for approximately 10-30 hours, preferably approximately 15-25 hours, for instance approximately 20-24 hours. The duration of the fermentation should be sufficient in order to provide the beneficial modified polyphenol containing plant material(s).

After completing the fermentation, the optional eliminating step f) of the polyphenol modifying strain of lactic acid bacteria takes place by heating, ultraviolet radiation, gamma radiation, pressure, electric current, electric discharge, pulsed electric fields, electric chock or sterile filtration. By eliminating the strain of lactic acid bacteria it will be possible to use the obtained mixture of modified polyphenol containing plant mixture free from lactic acid bacteria in any composition that can be taken by an individual.

The polyphenol containing plant material(s) which are modified by the fermentation of the strain of lactic acid bacteria are for example chosen from the group comprising fruits, vegetables, berries, tea, grains, green tea, coffee, cocoa, chocolate and bark. The fruits and berries are for example chosen from the group of blueberries, lingonberries, cranberries, apples, bananas, blackcurrant, strawberries, raspberries, rose hips, grapes, citrus, aronia, Japanese quince, sloe, rosehip and elderberry, olives, caper berries and other fruits rich in polyphenols. The bark is preferably chosen from cinnamon. The vegetables are for example chosen from beans. The invention is not limited to the above-mentioned specific examples. The important aspect in view of the chosen polyphenol containing plant material(s) is that the polyphenol containing plant material(s) to be used should be affected by the fermentation with the strain of lactic acid bacteria and providing a modified polyphenol containing plant material.

In the present context the phrase "modifying polyphenol containing plant materials" means that a fermentation of an added strain of lactic acid bacteria has taken place in the presence of a plant material containing polyphenols. The fermentation takes place and affects the present polyphenol groups to provide modified polyphenol containing plant material(s).

In the present context the term "modified polyphenol containing plant material(s)" is intended the product(s) as obtained after fermentation of the polyphenol containing plant material in the presence of a strain of lactic acid bacteria at the conditions as specified herein. In the experimental part the tested polyphenol containing material is blueberries, lingonberries and rose hip and it has been shown that it is only the test product containing blueberries, lingonberries and rose hip having been fermented that causes the significant effect of lower insulin responses, meaning that it is most probably the fermentation of the polyphenol containing materials that cause the lower insulin response. Thus, in accordance with the present invention the term "modified polyphenol containing plant material(s)" means such substances that are obtained after fermentation of the polyphenol containing plant materials. Such "modified polyphenol containing plant materials" should provide the desired effect of lowering the insulin responses in humans after intake of the same as compared to the intake of a polyphenol containing plant material, which has not been fermented with a strain of lactic acid bacteria. The lowering of the insulin level by the intake of modified polyphenol containing plant materials in any suitable form should be in the interval of approximately 1-50%, preferably approximately 5-40%, more preferably approximately 10-30%, even more preferably approximately 15-25%, for instance approximately 25%.

The invention further relates to the use of a mixture of modified polyphenol containing plant material(s) comprising living lactic acid bacteria or a mixture of modified polyphenol containing plant material(s) free from living lactic acid bacteria, for the manufacture of a composition for the prevention or treatment of diabetes, the metabolic syndrome, obesitas and cardiovascular diseases.

The composition is preferably a pharmaceutical composition or food composition. The food composition is for instance a food product or food supplement.

The food product could be chosen from the group comprising breads, cheeses, yogurts juices, health drinks, health bars, spreads, biscuits and cereals. It is convenient to include the mixture of modified polyphenol containing plant material(s) or the mixture of modified polyphenol containing plant material(s) free from living lactic acid bacteria in a food composition since such a composition is readily taken by an individual to stay healthy, and the cardiovascular diseases as mentioned above could be prevented.

Method and Material
Test Products

In order to show the effects of the present invention it has been tested to evaluate potential differences in postprandial blood glucose and insulin responses after intake of different compositions based on a polyphenol containing plant material such as blueberry and sucrose depending on 1) type and degree of heat treatment of the blueberry composition 2) the presence of lactic acid producing bacteria (*Lactobacillus plantarum* 299v and *Lactobacillus plantarum* HEAL 19, respectively) in the composition and 3) fermentation of the blueberry composition with *L. plantarum* HEAL 19.

Five different test drinks and a reference drink (Ref.) were included in the study. The test drinks consisted of one untreated unfermented blueberry drink (B-untr), one drink based on unfermented blueberries that had been pasteurized (B-past), two drinks which were pasteurized and unfermented with the addition of *Lactobacillus plantarum* 299v and HEAL 19, respectively, (B-299v and B-HEAL) and one drink that had been pasteurized and fermented (B-ferm) with *L. plantarum* HEAL 19. The reference drink consisted of glucose dissolved in water. The blueberries (*Vaccinium myrtillus*) were mixed to a purée, prior to storage at −20° C. After thawing, the blueberries were diluted with water (1:1) and homogenized for 5 minutes using a home mixer. Thereafter the blueberries were diluted a second time (1:1) obtaining a 25% blueberry solution. The blueberry solution was then homogenized at 25 000 rpm with a high performance disperser (Ultra Turrax T25, Janke & Kunkel IKA, Werke GmbH & Co. KG, Staufen, Germany). Samples for the unfermented blueberry drink were taken (B-untreated) and frozen at −20° C. until used in the meal study. The rest of the blueberry solution was pasteurized (94° C., 2 s) and stored at −20° C. (B-pasteurized).

The two drinks with the separate addition of *Lactobacillus plantarum* 299v (B-299v) and *Lactobacillus plantarum* HEAL 19 (B-HEAL 19) were prepared by thawing the B-pasteurized drink one day before the study and the respective *Lactobacillus* strain was added and thereafter the drink was allowed to stand over night in the refrigerator (+4° C.) until serving.

Approximately one week before being served, 600 ml of the pasteurized blueberry solution was fermented in a vessel, KOH was added to adjust pH to 5. Thereafter the blueberry solution was inoculated, using *Lactobacillus plantarum* HEAL 19 ($1 \times 10^7$ colony forming units (cfu)/ml). One gram of autoclaved broad bean flower was added as nitrogen source. The blueberry solution was left to ferment for 20 h until a final cfu of $1 \times 10^9$/ml (pH 3.8) was attained (B-fermented). After fermentation the blueberry solution was stored at 4° C. The fermentation was performed by Probi AB (Lund, Sweden). A glucose drink was used as reference meal containing 30 g D+-glucose (VWR international Ltd. Poole, England) to 300 ml water. All meals contributed with 30 g of carbohydrates. A loaf of wheat white bread (WWB, Dollar Storfranska, Lockarp, Sweden) was provided to each one of the test subjects on the onset of the study. An individually chosen amount of slices was to be ingested on the evening before each occasion.

Table 1 shows the different composition of the test drinks and reference.

TABLE 1

| | Drink amount (g) | Total amount of low molecular carbohydrates from berries (g) | Fructose from berries (g) | Glucose From berries (g) | Addition of glucose (g) | Addition of Sucrose (g) | Total amount Of carbohydrates (g) |
|---|---|---|---|---|---|---|---|
| Ref. | 300 | — | — | — | 30 | | 30 |
| B-unt.* | 300 | 3.82 | 2.19 | 1.63 | — | 26.18 | 30 |
| B-past.* | 300 | 3.82 | 2.19 | 1.63 | — | 26.18 | 30 |
| B-ferm.* | 300 | 2.64 | 2.03 | 0.61 | 1.18 | 26.18 | 30 |
| B-299v* | 300 | 3.82 | 2.19 | 1.63 | — | 26.18 | 30 |
| B-HEAL 19* | 300 | 3.82 | 2.19 | 1.63 | — | 26.18 | 30 |

The berries contained <0.04 sucrose.
*All blueberry drinks contained further 72.8 mg ascorbic acid, 320.1 mg trecomex, 291 mg CNK.

Before serving 72.8 ascorbic acid, 320.1 trecomex (modified potato starch), 291 mg CNK (carrageenan E407), and 26.18 g sucrose were added to each blueberry drink. In addition, 1.18 g glucose was added to the B-fermented drink to compensate for losses of this carbohydrate during fermentation. Finally, all blueberry drinks were adjusted with 32.0 g water so that 300 g blueberry drinks containing 20% blueberries and 30 g carbohydrates were obtained.

Test Drink Studies

All drinks were served as breakfasts and randomly provided, at least five days apart. Written informed consent was acquired from all subjects. They were also well aware of the fact that they could withdraw from the study at any time and without further explanation. The ethics committee of the faculty of medicine at Lund University approved the study.

Test Subjects

Fifteen healthy, non-smoking volunteers, 7 women and 8 men participated in the acute meal study. The average age was 25±2.4 (mean±SD) years and the mean body mass index was in the normal range (22.4±2.0 kg/m$^2$; mean±SD). The subjects were not receiving any drug treatment. They were asked to avoid alcohol intake, physical activity and a dinner rich in fibre the day before the test. The subjects ate an individually chosen amount of the WWB between 9 and 10 pm on the evening before each occasion. The individually chosen amount of slices was to be kept equal throughout the study. After the WWB meal, the subjects were asked not to ingest anything more before arriving at the laboratory. However, if necessary a small amount of water was allowed to be ingested after 10 pm. Each subject participated at four occasions, at least one week apart.

Study Design and Blood Sampling

The subjects arrived in the laboratory in the morning at 07.45 and a peripheral catheter was inserted into an antecubital vein. At each occasion all participants filled out a questionnaire concerning their physical condition for the day, including feelings of stress or anxiousness. The meal was consumed in a steady manner during 10 minutes. Capillary blood was collected for serum insulin and analysis of plasma blood glucose at fasting and at 15, 30, 60, 90, 120, 180, 240 minutes after meal ingestion.

Glucose Analysis

Blood glucose was determined with a B-Glucose Analyser (Hemocue 201+, Hemocue AB, Ängelholm, Sweden).

Insulin Analysis

The serum insulin samples were stored at −20° C. The analysis was performed on an integrated immunoassay analyzer (CODA Open Microplate System; Bio-Rad Laboratories, Hercules Calif.) by using an enzyme immunoassay kit (Mercodia Insulin Elisa; Mercodia AB, Uppsala, Sweden).

Calculations and Statistical Analysis

For each participant and each test drink, the incremental areas under the curve (AUCs) at 0-45 minutes and 0-120 minutes for blood glucose and serum insulin were calculated by using GraphPad PRISM (version 3.02; GraphPad Software Inc, San Diego). All areas below the baseline were excluded from the calculations. Blood glucose, and serum insulin, were statistically analyzed at each time point. The statistical calculations were performed with MINITAB Statistical Software (release 13.1 for windows). Significances were determined by general linear model (ANOVA), followed by Tukey's multiple comparisons test or Dunnett's test. Differences resulting in $P<0.05$ were considered significant.

Plasma Glucose

As well early (0-45 min) as late (0-90 min) areas under glucose curves were significantly lower after intake of the blueberry drinks compared to the glucose reference. The GI value for the blueberry drinks were well gathered in the interval 58-64 and significantly lower than the glucose reference (GI=100). The plasma glucose response is shown in FIG. 1.

TABLE 2

Plasma glucose after glucose reference and blueberry drinks which have been pasteurised, fermented and/or supplemented with bacteria.

| | | | Glucose | | |
|---|---|---|---|---|---|
| Drinks | n | Fasting value (mmol/L) | Peak value (delta) at 30 min (mmol/L) | Area under curve 0-45 min (mmol min/L) | GI (0-90 min) |
| Glucose | 15 | 5.2 ± 0.1 | 4.1 ± 0.3$^a$ | 115.6 ± 8.2$^a$ | 100 ± 0.0$^a$ |
| B-untr | 14 | 5.2 ± 0.1 | 3.0 ± 0.2$^b$ | 80.8 ± 7.2$^b$ | 58 ± 4.6$^b$ |
| B-past. | 13 | 5.2 ± 0.1 | 3.0 ± 0.3$^b$ | 82.4 ± 7.1$^b$ | 64 ± 5.5$^b$ |
| B-ferm. | 15 | 5.2 ± 0.1 | 2.8 ± 0.3$^b$ | 76.6 ± 8.0$^b$ | 61 ± 6.9$^b$ |
| B-299v | 14 | 5.3 ± 0.1 | 3.2 ± 0.2$^b$ | 81.1 ± 6.9$^b$ | 60 ± 4.7$^b$ |
| B-HEAL19 | 14 | 5.2 ± 0.1 | 2.9 ± 0.2$^b$ | 80.2 ± 5.3$^b$ | 63 ± 4.4$^b$ |

The figures indicate average values ± SD, n = number of test persons. Average values in the same column with different letters are significantly different ($P < 0.05$).

Serum Insulin

Figure 2:
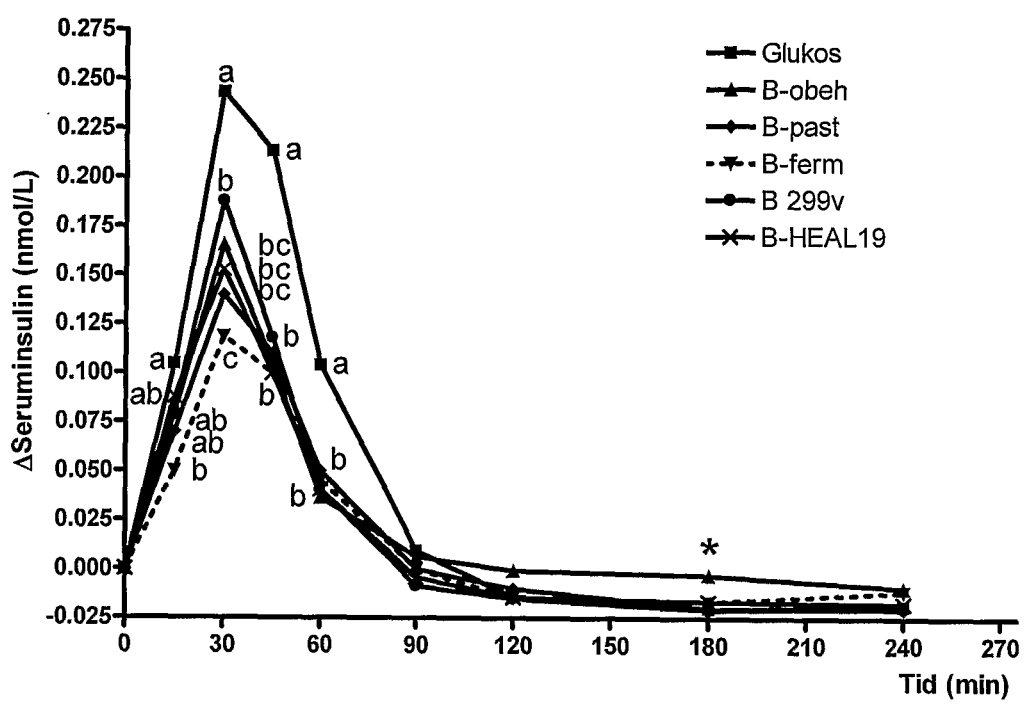
FIG. 2 shows the serum insulin responses after intake of different blueberry products subjected to different processes/additives compared to a glucose reference.
Figure 3:
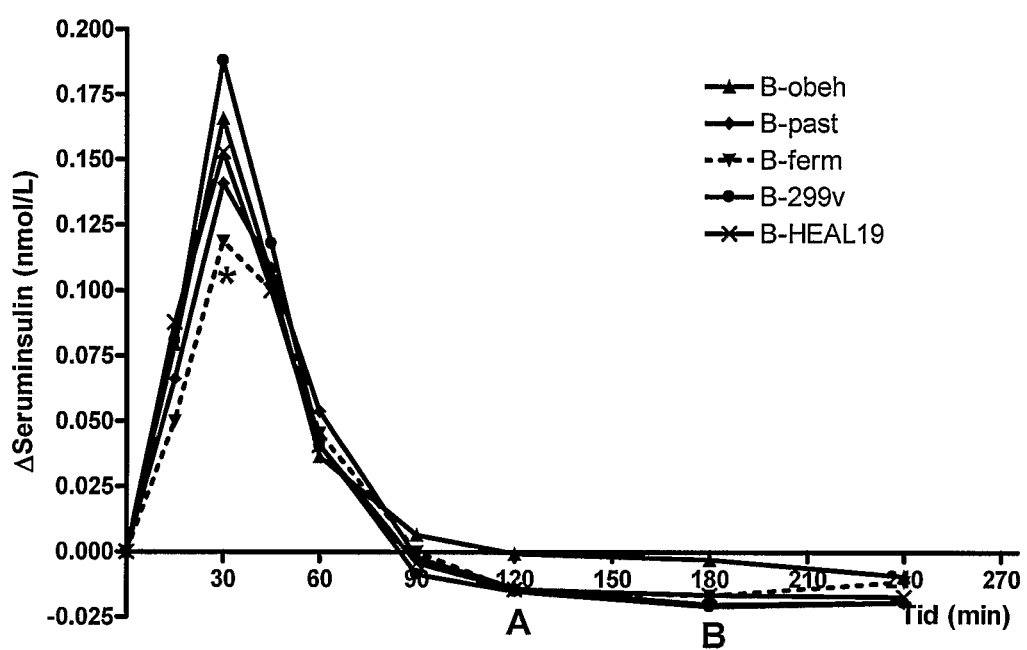
FIG. 3 shows the insulin responses after intake of different blueberry products subjected to different processes/additives compared to an untreated control (B-untreated). After 30 minutes the B-ferm gives a significant lower insulin response compared to control (B-untreated) (P<0.05, Dunnet's test with B-untreated as control).

The insulin responses after intake of the different blueberry drinks and references are shown in FIG. 2. In the interval 30-60 min all blueberry drinks gave rise to significantly lower insulin responses compared to the glucose reference. After 15 min the insulin level after intake of B-ferm was significantly lower compared to the glucose reference. In the early postprandial phase (expressed as 0-45 min AUC) B-ferm gave rise to lower insulin response than B-HEAL 19.

In order to study the importance of pasteurisation and fermentation (with *L. plantarum* HEAL 19) or addition of *Lactobacillus plantarum* to the blueberry raw material, the insulin responses of B-past, B-ferm, B-299v and B-HEAL 19 were compared to the untreated control drink (B-untr). At 30 min after intake B-ferm was significantly lower compared to B-untreated. At 120 min B-299v and B-HEAL 19 showed significantly lower insulin responses compared to B-untreated. A comparison of the early insulin response (0-45 min AUC) showed that B-ferm gave a significantly lower insulin response (25%) compared to untreated blueberry drink ($P<0.05$, Table 4). Neither pasteurisation or addition of *Lactobacillus plantarum* 299v or *Lactobacillus plantarum* HEAL 19, respectively, affected the postprandial insulin area significantly in relation to the untreated blueberry drink.

TABLE 3

Serum insulin responses of healthy test subjects after intake of glucose drink and drinks based on blueberry raw material subjected to pasteuristion, fermentation and/or supplemented with bacteria.

| Drinks | n | Fasting value (pmol/L) | Insulin Peak value (delta) at 30 min (pmol/L) | Area under curve 0-45 min (nmol min/L) | II (0-90 min) |
|---|---|---|---|---|---|
| Glucose | 15 | $43.3 \pm 2.2^{ab}$ | $243 \pm 30.3^{a}$ | $6.8 \pm 0.8^{a}$ | $100 \pm 0.0^{a}$ |
| B-untr | 14 | $33.8 \pm 6.2^{b}$ | $166 \pm 18.9^{bc}$ | $4.4 \pm 0.4^{bc}$ | $63 \pm 6.6^{b}$ |
| B-past | 13 | $47.2 \pm 6.7^{ab}$ | $141 \pm 21.6^{bc}$ | $3.9 \pm 0.5^{bc}$ | $56 \pm 3.2^{b}$ |
| B-ferm | 15 | $50.0 \pm 5.6^{a}$ | $119 \pm 17.8^{b}$ | $3.3 \pm 0.4^{c}$ | $46 \pm 3.7^{b}$ |
| B-299v | 14 | $49.3 \pm 7.8^{a}$ | $188 \pm 25.9^{c}$ | $4.9 \pm 0.8^{b}$ | $61 \pm 5.8^{b}$ |
| B-HEAL19 | 14 | $45.0 \pm 5.7^{ab}$ | $153 \pm 18.8^{bc}$ | $4.4 \pm 0.6^{bc}$ | $64 \pm 6.0^{b}$ |

The figures indicate average values ± SD, n = number of test persons. Average values in the same column with different letters are significantly different (P < 0.05).

Fermentation of blueberries using *Lactobacillus plantarum* HEAL19 seems to be a key factor for the reduced insulin response. The results suggest that the fermentation process improves insulin economy.

TABLE 4

Comparison of insuline response of pasteurized and fermented blueberry drink with untreated blueberry drink as control.

| Drinks | Area under curve 0-45 min (nmol min/L) | Difference in insulin response to B-Untreated (%) |
|---|---|---|
| B-untr | $4.4 \pm 0.4$ | — |
| B-past | $3.9 \pm 0.5$ | $-11$ |
| B-ferm | $3.3 \pm 0.4^{*}$ | $-25$ |

*Indicates signficant difference to control drink, B-untreated (P < 0.05, Dunnet's test with B-untreated as control drink.

The 25% lower insulin response after intake of the fermented blueberry drink with *Lactobacillus plantarum* HEAL 19 was not seen concomitant with a similar decrease in plasma glucose, since the postprandial plasma glucose responses after the blueberry drinks were at the same level. However, fermentation of blueberries using *Lactobacillus plantarum* HEAL19 seems to be a key factor of the reduced insulin response seen with drinks containing fermented blueberries. This effect is not seen when the same bacteria *Lactobacillus plantarum* HEAL 19 has been added to the blueberry drink just before intake. Thus, it is not the presence of the bacteria per se which gives rise to the reduced insulin response, but rather the fermentation itself that is important. The active mechanism causing this interesting effect could be due to the components produced or modified by the fermentation, i.e. modified polyphenol components available in the blueberries after fermentation.

In summary it can be concluded that the fermented blueberry drink reduced the insulin response with 25% compared to the unfermented blueberry drink. In the future, products aimed for people with metabolic disturbances could present an additional way of preventing and maybe also decreasing the development of type 2 diabetes and endothelial disturbances. Viewing the "metabolic disturbances epidemic" in a greater perspective, preferably done by integrating all aspects of the problem, i.e. not only nutritional and clinical but also social, cultural and economical, one might be able to introduce an over all healthy lifestyle in the western and in the developing countries. An increased knowledge of all consumers would hopefully get the industry to follow the desires of the market.

Test Comparing Effects for Drinks with Living Bacteria with Effects for Drinks with Eliminated Bacteria Two different test drinks were included in a study to evaluate if a drink where the culture of *L. plantarum* HEAL 19 is pasteurized after fermentation gives the same low insulin response as a drink where the culture of *L. plantarum* HEAL 19 is left alive after fermentation.

The test drinks consisted of one drink pasteurized and fermented with *L. plantarum* HEAL 19 and one drink that was pasteurized and fermented with *L. plantarum* HEAL 19 and then pasteurized after the fermentation. The blueberries (*Vaccinium myrtillus*) were mixed to a purée, prior to storage at −20° C. After thawing, the blueberries were diluted with water (1:1) and homogenized for 5 minutes using a home mixer. Thereafter the blueberries were diluted a second time (1:1) obtaining a 25% blueberry solution. The blueberry solution was then homogenized at 25 000 rpm with a high performance disperser (Ultra Turrax T25, Janke & Kunkel IKA, Werke GmbH & Co. KG, Staufen, Germany). Samples for the unfermented blueberry drink were taken (B-untreated) and frozen at −20° C. until used in the meal study. The rest of the blueberry solution was pasteurized (94° C., 2 s) and stored at −20° C. (B-past.).

Approximately one week before being served, 600 ml of the pasteurized blueberry solution was fermented in a vessel, KOH was added to adjust pH to 5. Thereafter the blueberry solution was inoculated, using *Lactobacillus plantarum* HEAL 19 ($1 \times 10^7$ colony forming units (cfu)/ml). One gram of autoclaved broad bean flower was added as nitrogen source. The blueberry solution was left to ferment for 20 h until a final cfu of $1 \times 10^9$/ml (pH 3.8) was attained. After fermentation the blueberry solution was stored at 4° C. or pasteurized again (94° C., 2 s) and stored at 4° C. The fermentation was performed by Probi AB (Lund, Sweden).

Table 5 shows the different composition of the test drinks.

TABLE 5

| | Drink amount (g) | Total amount of low molecular carbohydrates from berries (g) | Fructose from berries (g) | Glucose From berries (g) | Addition of Sucrose (g) | Total amount Of carbohydrates (g) |
|---|---|---|---|---|---|---|
| B-ferm.* alive | 300 | 2.64 | 2.03 | 0.61 | 26.18 | 29 |
| B-ferm. and pasteurized* | 300 | 2.64 | 2.03 | 0.61 | 26.18 | 29 |

The berries contained <0.04 sucrose.
*All blueberry drinks contained further 72.8 mg ascorbic acid, 320.1 mg trecomex, 291 mg CNK.

Before serving 72.8 mg ascorbic acid, 320.1 mg trecomex (modified potato starch), 291 mg CNK (carrageenan E407), and 26.18 g sucrose were added to each blueberry drink. In addition, 1.18 g glucose was added to the B-fermented drink to compensate for losses of this carbohydrate during fermentation. Finally, all blueberry drinks were adjusted with 32.0 g water so that 300 g blueberry drinks containing 20% blueberries and 30 g carbohydrates were obtained.

Test Drink Studies

All drinks were served as breakfasts and randomly provided, at least five days apart. Written informed consent was acquired from all subjects. They were also well aware of the fact that they could withdraw from the study at any time and without further explanation. The ethics committee of the faculty of medicine at Lund University approved the study.

Test Subjects

Thirteen healthy, non-smoking volunteers participated in the acute meal study. The average age was 25.5±1.34 (mean±SD) years and the mean body mass index was in the normal range (20.8±0.24 kg/m$^2$; mean±SD). One of the subjects suffered from gastric influenza the days before one test occasion and was therefore excluded from the study. The subjects were not receiving any drug treatment. They were asked to avoid alcohol intake, physical activity and a dinner rich in fibre the day before the test. The subjects ate an individually chosen amount of the WWB between 9 and 10 pm on the evening before each occasion. The individually chosen amount of slices was to be kept equal throughout the study. After the WWB meal, the subjects were asked not to ingest anything more before arriving at the laboratory. However, if necessary a small amount of water was allowed to be ingested after 10 pm. Each subject participated at four occasions, at least one week apart.

Study Design and Blood Sampling

The subjects arrived in the laboratory in the morning at 07.45 and a peripheral catheter was inserted into an antecubital vein. At each occasion all participants filled out a questionnaire concerning their physical condition for the day, including feelings of stress or anxiousness. The meal was consumed in a steady manner during 10 minutes. Capillary blood was collected for serum insulin and analysis of plasma blood glucose at fasting and at 15, 30, 60, 90, 120 minutes after meal ingestion.

Glucose Analysis

Blood glucose was determined with a B-Glucose Analyser (model no. 120401, Hemocue AB, Ängelholm, Sweden).

Insulin Analysis

The serum insulin samples were stored at −20° C. The analysis was performed on an integrated immunoassay analyzer (CODA Open Microplate System; Bio-Rad Laboratories, Hercules Calif.) by using an enzyme immunoassay kit (Mercodia Insulin Elisa; Mercodia AB, Uppsala, Sweden).

Calculations and Statistical Analysis

For each participant and each test drink, the incremental areas under the curve (AUCs) at 0-45 minutes and 0-120 minutes for blood glucose and serum insulin were calculated by using GraphPad PRISM (version 3.02; GraphPad Software Inc, San Diego). All areas below the baseline were excluded from the calculations. Blood glucose, and serum insulin, were statistically analyzed at each time point. The statistical calculations were performed with MINITAB Statistical Software (release 13.1 for windows). Significances were determined by general linear model (ANOVA), followed by Tukey's multiple comparisons test or Dunnett's test. Differences resulting in P<0.05 were considered significant.

Plasma Glucose

Figure 4:
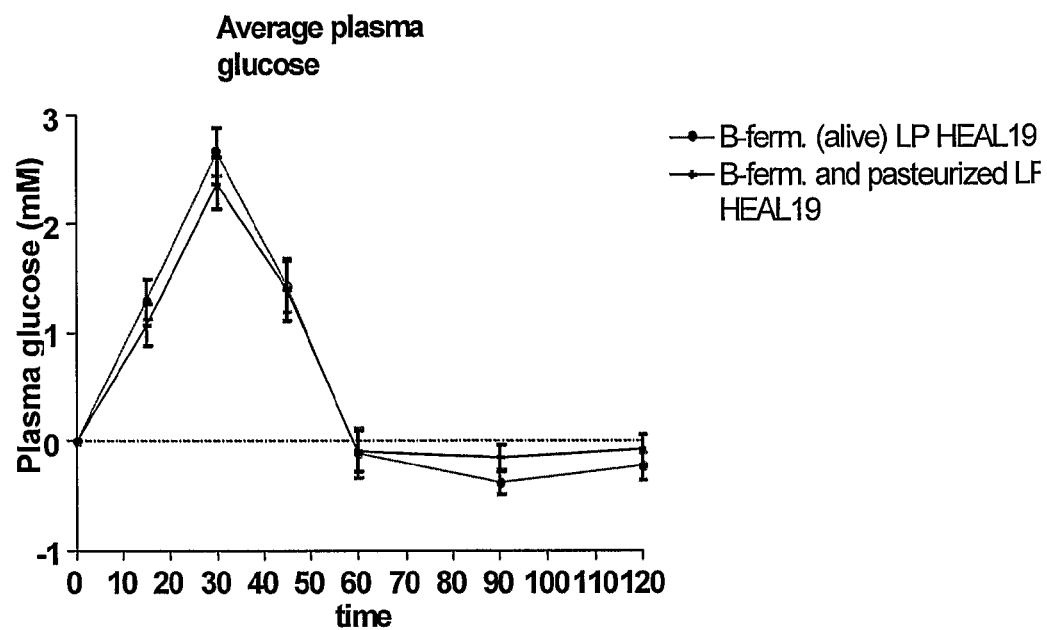
FIG. 4 shows the postprandial plasma glucose curves obtained after intake of a fermented blueberry drink with living bacteria and a fermented blueberry drink where the bacteria thereafter are killed by pasteurization.

As well early (0-45 min) as late (0-120 min) areas under glucose curves were slightly lower after intake of the test drink that was pasteurized after fermentation compared to the test drink with living bacteria, as can be seen in FIG. 4. The profile of the glucose curve has been analyzed by dividing the period that blood glucose stays above fasting value with the maximal increase in blood glucose from the fasting value. This quotient is called glucose Duration/Peak quota (min/Δ mM). A high value on the glucose Duration/Peak quota means that the glucose curve is long and low and a low value indicates an unfavourable curve profile with a short and high curve. No GI value could be determined since no reference was included in this test.

TABLE 6

AUC 120 min (plasma glucose) for fermented drink with living bacteria and fermented and pasteurized drink

| Drinks | AUC 120 min. | SEM (n = 12) |
|---|---|---|
| B-ferm. alive | 85.86 | 8.13 |
| B-ferm. and pasteurized | 81.43 | 9.10 |

The figures indicate average values ± SD, n = number of test persons.

TABLE 7

AUC 45 min (plasma glucose) and glucose Duration/Peak quota for fermented drink with living bacteria and fermented and pasteurized drink

| Drinks | AUC 45 min. | SEM (n = 12) | Neg AUC 30-120 min | SEM (n = 12) | Glucose Duration/Peak quota | SEM (n = 12) |
|---|---|---|---|---|---|---|
| B-ferm. alive | 69.90 | 6.11 | 22.65 | 4.93 | 26.36 | 3.21 |
| B-ferm. and pasteurized | 62.28 | 5.93 | 16.66 | 4.50 | 29.21 | 3.21 |

The figures indicate average values ± SD, n = number of test persons.

Serum Insulin

Figure 5:
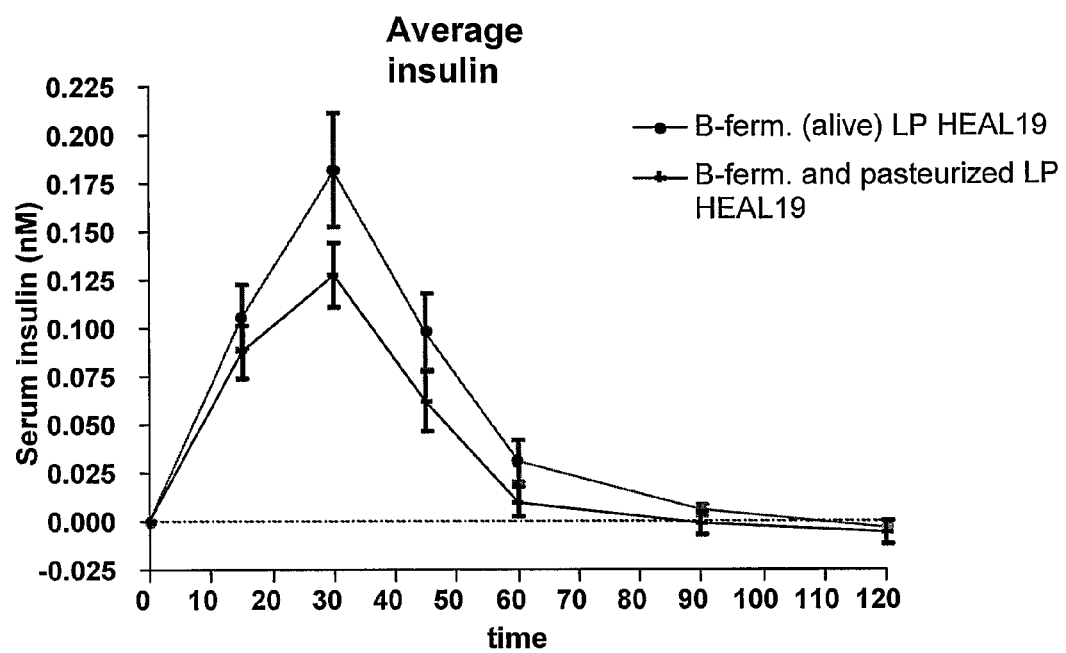
FIG. 5 shows the insulin responses after intake of a fermented blueberry drink with living bacteria and a fermented blueberry drink where the bacteria thereafter are killed by pasteurization.

The insulin responses after intake of the two blueberry drinks are shown in FIG. 5. The AUC was lower after intake of the test drink that was pasteurized after fermentation compared to the test drink with living bacteria. No II value could be determined since no reference was included in this test.

TABLE 8

AUC 120 min (serum insulin responses) for fermented drink with living bacteria and fermented and pasteurized drink

| Drinks | AUC 120 min | SEM (n = 12) |
|---|---|---|
| B-ferm. alive | 6.65 | 1.06 |
| B-ferm. and pasteurized | 4.75 | 0.51 |

The values have been transformed with Box Cox Transformation before analysis

Discussion

Both drinks gave approximately the same response for glucose. The drink that was pasteurized, i.e. the bacteria were killed, showed better results on the insulin response than the drink with living bacteria. In the earlier study no effect was seen from the pasteurization alone on the insulin response, i.e. pasteurized blueberries gave the same result as non-pasteurized blueberries. The present study indicates, however, that the degree of heat treatment after fermentation to a large extent may affect the insulin response.

The mechanism for this effect need to be evaluated further. One theory is that a more powerful heat treatment, through effects on polyphenols and other bioactive components in the blueberries, gives an insulin lowering effect which is illustrated by the drink with heat killed bacteria due to the extra step of heat treatment.

Phenolic Compounds Analysis

In order to provide evidence that a modification of the polyphenol containing plant materials take place a study was conducted comparing the contents of catechine, epicatechine, proanthocyanidin dimer aglycone, proanthocyanidin trimer aglycone, proanthocyanidin tetramer aglycone, 3,4-dihydroxyphenylpropionic acid, L-(−)-3-phenyl lactic acid, protocatechuic acid and cyanidin-3-galactoside/cyanidin-3-glucoside in rosehip purée, blueberry, blueberry peel and lingonberry peel before and after fermentation.

All fruit fractions were pasteurized before fermentation in order to avoid that other microorganisms should affect the fermentation.

For the analysis of phenolic compounds samples were weighed and a solution for extraction was added (concentration in the sample: 50% ethanol, 0.05M phosphoric acid alternatively 50% methanol, 0.5%). Thereafter, the samples were extracted for 10 min in an ultrasonic bath and then centrifuged, after which the supernatant was transferred to vials and analysed by HPLC-MS analysis. The HPLC-MS analysis was performed as in Salminen et al. Characterisation of proanthocyanidin aglycones and glycosides from rose hips by high-performance liquid chromatography-mass spectrometry, and their rapid quantification together with Vitamin C. *J Chrom A* 2005; 1077:170-180, and Salminen et al. Characterisation of hydrolysable tannins from leaves of *Betula pubescens* by high-performance liquid chromatography-mass spectrometry. *J Chrom A* 1999; 864: 283-291 by a API 150 EX Turbo Ionspray.

The instrument was set in a negative mode, i.e. the negative iones were analysed. The HPLC-system consisted of an HPLC pump of the type PerkinElmer LC-200 Micro Pump and also a PerkinElmer 200 Auto sampler. The injection volume of the samples was 8 µl.

Scanning was conducted over the mass numbers between 90-1000 m/z.

Specific mass numbers used for detection:

Catechin, m/z 289 (M-H)

Epicatechin, m/z 289 (M-H)

Procyanidin B2, m/z 577 (M-H)

Proanthocyanidin dimer aglycone, m/z 577 (M-H)

Proanthocyanidin trimer aglycone, m/z 865 (M-H)

Proanthocyanidin tetramer aglycone, m/z 1153 (M-H)

3,4-dihydroxyphenylpropionic acid, m/z 181 (M-H)

L-(−)-3-phenyllactic acid, m/z 165 (M-H)

Protocatechuic acid, m/z 153 (M-H)

Cyanidin-3-galactoside, Cyanidin-3-glucoside, m/z 447 (M-H)

Figure 6:
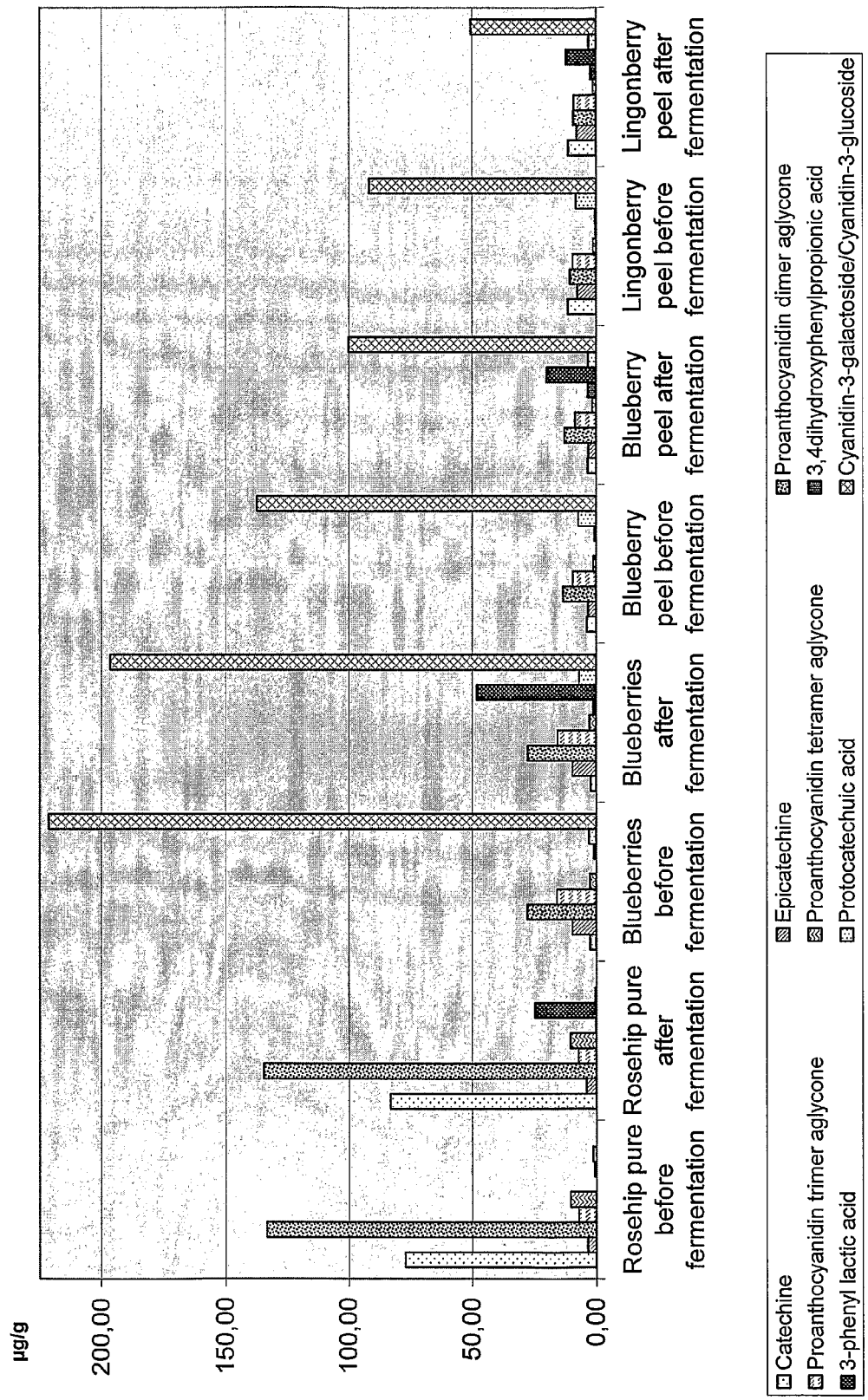
FIG. 6 shows the contents of catechine, epicatechine, proanthocyanidin dimer aglycone, proanthocyanidin trimer aglycone, proanthocyanidin tetramer aglycone, 3,4-dihydroxyphenylpropionic acid, 3-phenyl lactic acid, protocatechuic acid and cyanidin-3-galactoside/cyanidin-3-glucoside in rosehip purée, blueberry, blueberry peel and lingonberry peel before and after fermentation.

The results of the study can be seen in FIG. 6, showing that the modification of polyphenol containing plant materials take place in both blueberries as well as in lingonberries and rose hip.

TABLE 9 modification of polyphenol containing plant material in blueberries, lingonberries and rose hip

| | Catechin µg/g FV | Epicatechine µg/g FV | Procyanidin B2 µg/g FV | Proanthocyanidin trimer aglycone µg/g FV | Proanthocyanidin tetramer aglycone µg/g FV | 3,4dihydroxyphenylpropionic acid µg/g FV | L-(−)-3-phenyllactic acid µg/g FV | Protocatechuic acid µg/g FV | Cyanidin-3-galactoside/Cyanidin-3-glucoside µg/g FV |
|---|---|---|---|---|---|---|---|---|---|
| Rosehip puree before fermentation | 77.05 | 3.44 | 133.19 | 7.07 | 10.37 | 0.01 | 0.65 | 1.23 | ND |
| Rosehip puree after fermentation | 83.01 | 3.86 | 134.49 | 7.22 | 10.52 | 0.24 | 24.63 | 0.44 | ND |
| Blueberries before fermentation | 2.47 | 9.64 | 27.63 | 15.68 | 2.58 | 0.01 | 0.95 | 2.93 | 221.44 |
| Blueberries after fermentation | 2.30 | 9.64 | 27.56 | 15.45 | 2.79 | 1.41 | 48.03 | 6.89 | 196.48 |
| Blueberry peel before fermentation | 3.80 | 3.19 | 13.31 | 9.40 | 1.18 | 0.02 | 0.65 | 7.22 | 137.24 |
| Blueberry peel after fermentation | 3.39 | 3.19 | 12.61 | 8.45 | 1.59 | 3.34 | 19.81 | 3.20 | 100.00 |
| Lingonberry peel before fermentation | 11.34 | 7.66 | 10.55 | 9.44 | 1.28 | 0.20 | 0.45 | 8.12 | 91.75 |
| Lingonberry peel after fermentation | 11.15 | 7.85 | 9.11 | 8.95 | 1.30 | 2.45 | 12.17 | 3.01 | 50.45 |

In a study on rats it has been shown that the concentration of selected phenolic compounds in the caecum were different if rosehip plus *Lactobacillus plantarum* 299v or *Lactobacillus plantarum* HEAL 19 were consumed in comparison with if only roship were consumed (Table 10). This indicate that the polyphenol components were modified during the fermentation in the caecum.

TABLE 10

Selected phenolic compounds in the cecal content. Peak 1 = µg catechin/g fresh weight, peak 2, 3, 4 and 6 = µg catechin equivalents/g fw, peak 5 = µg quercetin-rhamnoside/g fw.

| | Peak 1 Catechin Rt 13.8 min, m/z 289 | Peak 2 Rt 16.1 min, m/z 291 | Peak 3 Rt 17.1 min, m/z 385 | Peak 4 Rt 18.6 min, m/z 291 | Peak 5 Rt 23.1 min, m/z 447 | Peak 6 Rt 29.3 min, m/z 289 |
|---|---|---|---|---|---|---|
| Colitis control | 1.6 | 5.3 | 0 | 1.7 | 0.6 | 9.3 |
| Lp299v | 0.9 | 5.8 | 0 | 3.3 | 1.0 | 8.2 |
| HEAL 19 | 1.2 | 5.4 | 0 | 2.2 | 0.8 | 2.4 |
| Rose hip | 29.9 | 122.7 | 100.8 | 12.2 | 0.2 | 8.6 |
| Rose hip + Lp299v | 38.7 | 119.8 | 51.5 | 11.3 | 0.2 | 18.2 |
| Rose hip + HEAL 19 | 40.9 | 134.2 | 28.2 | 17.1 | 0.2 | 64.4 |

Test Comparing Fermentation with *Lactobacillus plantarum* HEAL 19, *Lactobacillus plantarum* 299v or *Pediococcus acidilactici*

In order to provide evidence that a modification of the polyphenol containing plant materials take place when fermenting with other bacteria a study was conducted comparing the contents of catechine, epicatechine, procyanidin B2, proanthocyanidin trimer aglycone, proanthocyanidin tetramer aglycone, 3,4-dihydroxyphenylpropionic acid, L-(−)-3-phenyl lactic acid, protocatechuic acid and cyanidin-3-galactoside/cyanidin-3-glucoside in blueberries before and after fermentation with *Lactobacillus plantarum* HEAL 19, *Lactobacillus plantarum* 299v or *Pediococcus acidilactici*.

Figure 7:
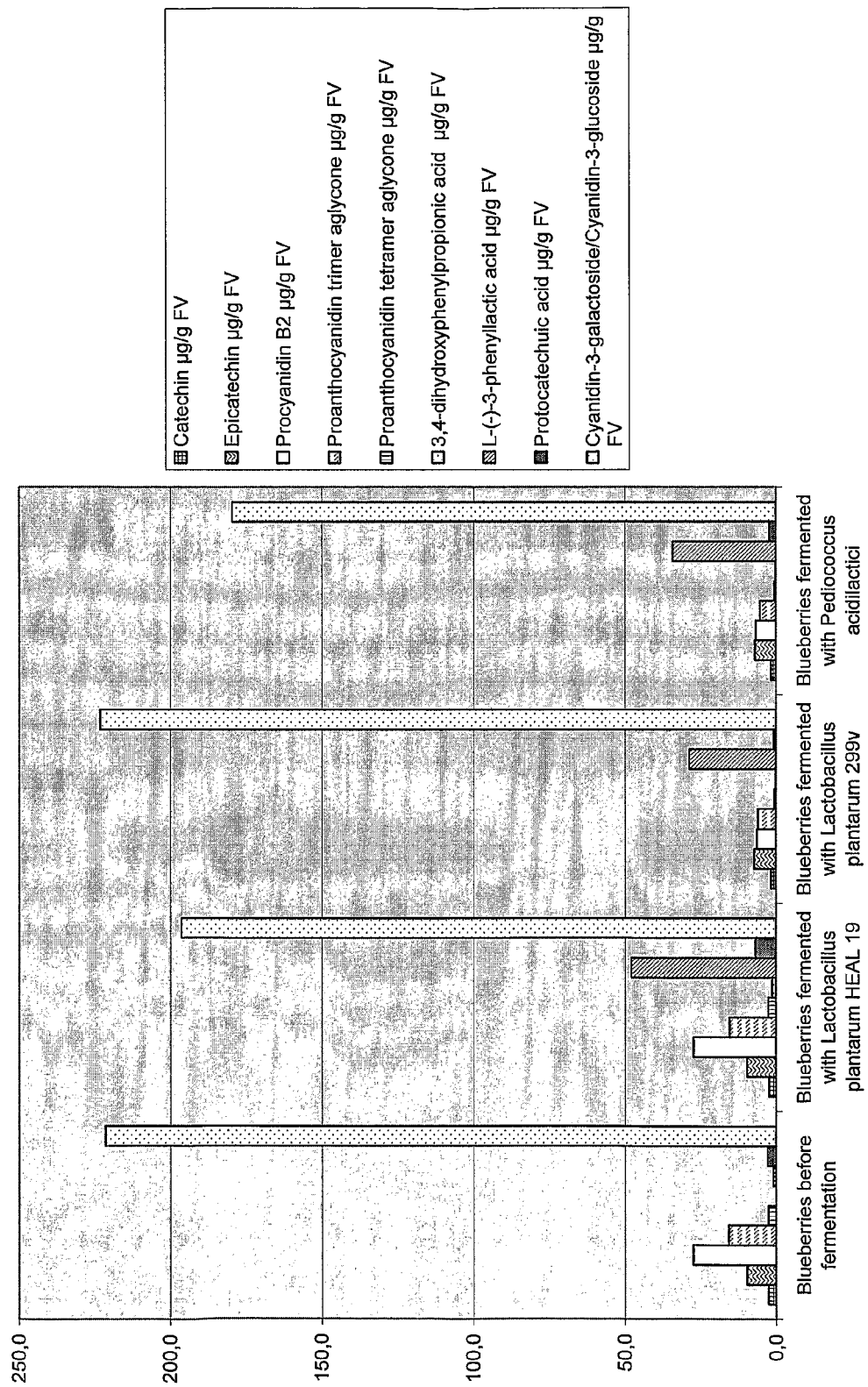
FIG. 7 shows the contents of catechine, epicatechine, procyanidin B2, proanthocyanidin trimer aglycone, proanthocyanidin tetramer aglycone, 3,4-dihydroxyphenylpropionic acid, L-(−)-3-phenyllactic acid, protocatechuic acid and cyanidin-3-galactoside/cyanidin-3-glucoside in blueberries before fermentation and after fermentation with *Lactobacillus plantarum* HEAL 19, *Lactobacillus plantarum* 299v or *Pediococcus acidilactici*.

The results of the study can be seen in FIG. 7, showing that the modification of polyphenol containing plant materials take place after fermentation with all the tested bacteria, i.e. *Lactobacillus plantarum* HEAL 19, *Lactobacillus plantarum* 299v or *Pediococcus acidilactici*.

TABLE 11 modification of polyphenol containing plant materials after fermentation with *Lactobacillus plantarum* HEAL 19, *Lactobacillus plantarum* 299v or *Pediococcus acidilactici*

| | Catechin µg/g FV | Epicatechine µg/g FV | Procyanidin B2 µg/g FV | Proanthocyanidin trimer aglycone µg/g FV | Proanthocyanidin tetramer aglycone µg/g FV | 3,4-dihydroxy-phenylpropionic acid µg/g FV | L-(−)-3-phenyllactic acid µg/g FV | Protocatechuic acid µg/g FV | Cyanidin-3-galactoside/Cyanidin-3-glucoside µg/g FV |
|---|---|---|---|---|---|---|---|---|---|
| Blueberries before fermentation | 2.5 | 9.6 | 27.6 | 15.7 | 2.6 | 0.0 | 0.9 | 2.9 | 221.4 |
| Blueberries fermented with *Lactobacillus plantarum* HEAL 19 | 2.3 | 9.6 | 27.6 | 15.4 | 2.8 | 1.4 | 48.0 | 6.9 | 196.5 |
| Blueberries fermented with *Lactobacillus plantarum* 299v | 1.8 | 7.3 | 6.5 | 6.1 | 0.7 | 0.1 | 29.0 | 0.9 | 223.2 |
| Blueberries fermented with *Pediococcus acidilactici* | 1.6 | 7.0 | 6.7 | 5.4 | 0.7 | 0.1 | 34.3 | 2.1 | 179.5 |

The invention claimed is:

1. A method of lowering insulin response in a subject having diabetes, metabolic syndrome or obesity, comprising administering to the subject a fermented blueberry mixture in an amount effective for lowering insulin response in said subject, wherein said fermented blueberry mixture is prepared by a method comprising:
   (a) mixing and homogenizing *Vaccinium myrtillus* blueberries and water to provide a homogenized mixture;
   (b) heating the homogenized mixture to 90° C. to 100° C. to eliminate bacterial species present to provide a heated mixture;
   (c) adding *Lactobacillus plantarum* HEAL 19 and at least one protein source selected from the group consisting of peptones, tryptones, yeast extracts and combinations thereof to the heated mixture to provide a fermentation mixture; and
   (d) fermenting the fermentation mixture for 10-30 hours at a temperature of 30° C.-50° C. to create a fermented blueberry mixture;
   wherein the insulin response in said subject, to which said fermented blueberry mixture has been administered, is lowered relative to an insulin response in an individual to whom said fermented blueberry mixture has not been administered.

2. The method according to claim 1, wherein said fermented blueberry mixture is in a pharmaceutical composition or food composition.

3. The method according to claim 2, wherein the food composition is a food product or food supplement.

4. The method according to claim 3, wherein said food product is selected from the group consisting of breads, cheeses, yogurts, juices, health drinks, health bars, spreads, biscuits and cereals.

5. The method of claim 1, wherein the *Lactobacillus plantarum* HEAL 19 is added in an amount of about $10^5$-$10^9$ cfu/ml mixture.

6. The method of claim 1, wherein the at least one protein source is added in amount of 0.0001-0.1% by weight of the mixture.

7. The method of claim 1, wherein the fermentation proceeds until a pH value of <5 is reached.

8. The method of claim 1, further comprising pasteurizing the fermented blueberry mixture obtained in (d).

* * * * *